United States Patent [19]

Moss et al.

[11] Patent Number: 5,126,251
[45] Date of Patent: Jun. 30, 1992

[54] STABLE MAMMALIAN CELL LINE EXPRESSING A BACTERIOPHAGE RNA POLYMERASE

[75] Inventors: Bernard Moss, Bethesda; Orna Elroy-Stein, Rockville, both of Md.

[73] Assignee: The United States of America as represented by the Secretary of the Department of Health and Human Services, Washington, D.C.

[21] Appl. No.: 485,871

[22] Filed: Mar. 1, 1990

Related U.S. Application Data

[63] Continuation-in-part of Ser. No. 376,687, Jul. 7, 1989, which is a continuation-in-part of Ser. No. 905,253, Sep. 3, 1986, abandoned.

[51] Int. Cl.$^5$ .................... C12N 15/00; C12N 5/10; C12P 21/00
[52] U.S. Cl. .............................. 435/69.1; 435/240.2; 935/34; 935/60; 935/70
[58] Field of Search ............... 435/69.1, 240.1, 240.2; 935/34, 60, 66, 70

[56] References Cited

PUBLICATIONS

Fundamental Virology, Second Edition, Raven Press, New York (1991), pp. 410, 776, & 777.
Lieber et al. High level game expression in mammalian cells by a nuclear T7-phage RNA polymerase, Nucleic Acids Research vol. 17, pp. 8485-8493 (1989).
Zhou et al., Synthesis of Functional mRNA in Mammalian Cells by Bacteriophage T3 RNA Polymerase, Molecular and Cellular Biology, Sep. 1990, vol. 10, pp. 4529-4537.
Elroy-Stein et al. Cytoplasmic expression system based on constitutive synthesis of bacteriophage T7 RNA polymerase in mammalian cells, Proc. Natl. Acad. Sci. USA vol. 87, pp. 6743-6747, Sep. 1990 Biochemistry.

*Primary Examiner*—Robert A. Wax
*Assistant Examiner*—S. L. Nolan
*Attorney, Agent, or Firm*—Cushman, Darby & Cushman

[57] ABSTRACT

The present invention relates to a eukaryotic cell line which expresses a foreign RNA polymerase gene. The invention further relates to a method of expressing a foreign protein in a eukaryotic environment utilizing the cell line. The present invention allows for the expression of a foreign protein in a eukaryotic cell without requiring transfecting or infecting the cell with a vector carrying the RNA polymerase gene.

13 Claims, 4 Drawing Sheets

Exp. 4 x O.N.

STABLE MAMMALIAN CELL LINE EXPRESSING A BACTERIOPHAGE RNA POLYMERASE

BACKGROUND OF THE INVENTION

This application is a continuation-in-part of the pending application Ser. No. 376,687 filed July 7, 1989 now allowed which, in turn, is a continuation-in-part of the pending application Ser. No. 905,253 filed Sep. 3, 1986, now abandoned Both applications 376,687 and 905,253 are incorporated herein by reference.

FIELD OF THE INVENTION

The present invention relates to a eukaryotic cell line expressing a foreign RNA polymerase and further, to a method of expressing foreign proteins in the eukaryotic cell line.

BACKGROUND INFORMATION

A cytoplasmic based transcription system which uses a recombinant vaccinia virus expressing bacteriophage T7 RNA polymerase was described previously [Fuerst et al., Proc. Natl. Acad. Sci. USA 83, 8122–8126 (1986)]. When a plasmid containing a T7 promoter regulated gene was transfected into such vaccinia infected cells, the gene was transcribed and protein was made. Still higher expression was obtained when the T7 promoter regulated gene was incorporated into a second vaccina virus and cells were coinfected with the latter and the T7 RNA polymerase containing virus [Fuerst et al., Mol. Cell. Biol. 7, 2538–2544 (1987)]. A further improvement in expression was obtained by adding the encephalomyocarditis untranslated leader sequence downstream of the T7 promoter [Elroy-Stein et al., Proc. Natl. Acad. Sci. USA 86, 6126–6130 (1989)]. This permitted cap-independent translation.

In a previous study [Dunn et al., Gene 68, 259–266 (1988)], T7 RNA polymerase made in vitro was injected into monkey cells but the enzyme was not made in the cell nor was it shown to make functional mRNA. In another study, [Chen et al., Cell 50, 1047–1055 (1987)] yeast were transformed with the T7 RNA polymerase gene and RNA but no protein was made. In a very recent report, Deuschle et al. [Proc. Natl. Acad. Sci. USA 86, 5400–5404 (1989)] made a stable transformed rabbit cell line that expressed T3 RNA polymerase which is very similar to T7 RNA polymerase. DNA transfected into these cells was transcribed but no protein was detected unless the cells were infected with vaccinia virus which presumably supplied capping enzyme needed for translation.

The present invention represents a major improvement in the field and involves the construction of a stable mammalian cell line that expresses a foreign RNA polymerase gene. For transient expression assays, this cell line eliminates the requirement for the vaccinia virus containing the T7 RNA polymerase gene. This is important because vaccinia virus causes a cytopathic effect and is also a health hazard. Alternatively, the cell line can be infected with a single recombinant vaccinia virus containing the T7 promoter regulated foreign gene and dispense with the requirement for a second vaccinia virus containing the T7 RNA polymerase. This simplifies the expression system particularly for large scale work in which it is inefficient to infect cells with two viruses simultaneously.

SUMMARY OF THE INVENTION

It is an object of the present invention to provide a cell line that expresses a foreign RNA polymerase gene.

It is another object of the present invention to provide a eukaryotic cytoplasmic based transcription system that does not require infection with virus.

Further objects and advantages of the present invention will be apparent hereinafter in connection with the description of the invention which follows.

In one embodiment, the present invention relates to a eukaryotic cell comprising:
  i) a foreign RNA polymerase gene; and
  ii) a construct comprising:
    a) a promoter recognized by the protein product of the foreign RNA polymerase gene;
    b) a DNA sequence that codes for an untranslated region of a RNA that confers cap independent translation; and
    c) a gene encoding a protein to be expressed;
wherein the promoter (a) and the DNA sequence (b) are operably linked to the gene (c).

In another embodiment, the present invention relates to a method of expressing a gene in a eukaryotic cell expressing a foreign RNA polymerase gene, which method comprises introducing into the cell a construct comprising:
  a) a promoter recognized by the protein product of the foreign RNA polymerase gene;
  b) a DNA sequence that codes for an untranslated region of a RNA that confers cap independent translation; and
  c) a gene encoding a protein to be expressed;
wherein the promoter (a) and the DNA sequence (b) are operably linked to the gene (c) under conditions such that the gene is expressed.

DETAILED DESCRIPTION OF THE INVENTION

Figure 1:
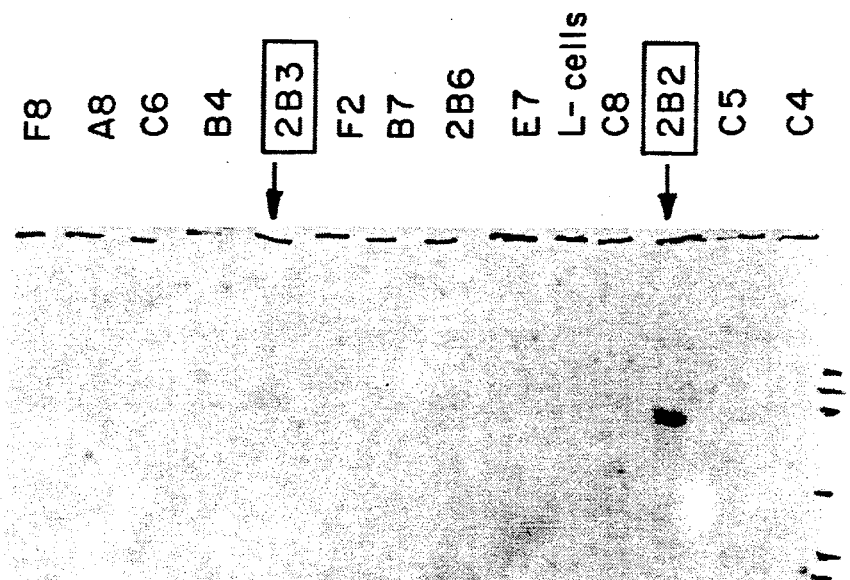
FIG. 1 shows 2 G418-resistant clones, 2B2 and 2B3, which are able to produce T7 RNA polymerase mRNA.

The present invention relates to a eukaryotic cell line, preferably a mammalian cell line such as a mouse L-cell line, Vero cell line or CHO cell line, which expresses a foreign RNA polymerase gene. Furthermore, the present invention relates to a method of expressing foreign proteins in such a eukaryotic cell line.

In one embodiment, the present invention relates to a mammalian cell line, advantageously a mouse L-cell line, that expresses a foreign RNA polymerase, advantageously a T7 RNA polymerase, in its cytoplasm. The cell line is capable of transcribing and translating a foreign gene provided the encoding DNA is lead by a promoter responsive to the RNA polymerase, advantageously the T7 promoter, followed by a cDNA copy of an untranslated region of a RNA that confers cap independent translation.

Foreign RNA polymerases for use in the present invention are preferably bacteriophage polymerases such as, for example, the RNA polymerase of the T7, SP6, GHI and T3 bacteriophage. One skilled in the art will appreciate that the promoter chosen to lead the foreign gene to be expressed depends on the RNA polymerase expressed by the cell line.

A viral untranslated region which confers cap independent translation is employed in the present invention. Viruses containing such an untranslated region include, but are not limited to, poliovirus, mengovirus, adenovirus and preferably, encephalomyocarditis virus.

The foreign gene to be expressed by the cell line can be present in a plasmid which is transfected into the cell line using known methods or, alternatively, it may be incorporated into a DNA based cytoplasmic virus which is then used to infect the cell line. Such DNA based cytoplasmic viruses for use in the present invention include, but are not limited to, poxviruses such as rabbit pox virus, cowpox virus, shope fibroma virus, ectomelia virus and vaccinia virus, and iridoviruses such as swine fever virus.

EXAMPLES

For purposes of illustrating a preferred embodiment of the present invention, in the following non-limiting examples, a mouse L-cell line expressing the T7 RNA polymerase will be discussed in detail. It is, however, to be understood that the discussion with respect to the mouse L-cell line generally applies to other eukaryotic cells especially mammalian cells, and with respect to the T7 RNA polymerase generally applies to other RNA polymerases, especially bacteriophage RNA polymerases.

Construction of Plasmids

Bacteriophage T7 RNA polymerase is encoded in T7 gene-1. Plasmid pTF7Gene-1 was constructed by cloning the 2.6Kb BamHI fragment from pAR1173 [Davanloo et al. Proc. Natl. Acad. Sci. USA 81, 2035-2039 (1984)]into the BamH1 site of M13mp19 followed by mutagenesis to modify the upstream sequence of T7Gene-I. The sequence immediately flanking the initiating ATG of T7Gene-1 was changed to 5'-GAATT-CAGATCTTAAATG-3' resulting in elimination of the prokaryotic ribosomal binding site and addition of EcoR1 and BglII sites downstream to the BamH1 site. pOSV-T7RP was constructed by ligating the filled-in 2.6Kb BamHI fragment from pTF7Gene-1 to the filled-in 4.3Kb HindIII-BglII fragment of pSV2-DHFR [Canaani & Berg, Proc. Natl. Acad. Sci. USA 79, 5166-5170 (1982)].

Generation of Mouse L(A9) Cell Line Containing Integrated Plasmids

Mouse L(A9) cells were cotransfected with supercoiled plasmids pOSV-T7RP and pSV2-Neo [Southern & Berg, J. Molec. App. Genet. 1, 327-342 (1982)]in a molar ratio of 10:1 respectively, using the calcium-phosphate coprecipitation technique [Graham & Van der Eb, Virology 52 456-467 (1973); and Wigler et al., Cell 14, 725-731 (1978)]. Osmotic shock of 15% glycerol was applied 6 hrs. later, and 24 hrs. thereafter the cells were split and replated in medium containing 400 μg active G418 per ml (Geneticin, from Gibco). G418 resistant colonies were isolated and maintained in medium containing half the G418 concentration used for selection.

Expression of T7 RNA Polymerase in Mouse L Cells

The expression of T7 RNA polymerase by the G418 resistant clones was analyzed in two ways. First, the ability of the cells to synthesize T7 RNA polymerase mRNA was checked. Total cellular RNA was isolated by a method described by Chromczynski & Sacchi [Anal. Biochem. 162, 156-159 (1987)].

10 μg RNA from each clone was fractioned on formaldehyde-agarose gels by the method of Lehrach et al. [Biochemistry 16, 4743-4751 (1977)], and then transferred to nitrocellulose and hybridized to $^{32}$P-labeled 2.6 Kb fragment from pAR1173 as described by Thomas [Proc. Natl. Acad. Sci. USA 81, 2035-2039 (1980)]. It was found that only 2 out of 35 G418-resistant clones were able to produce T7 RNA polymerase mRNA (2600 nt in length). (FIG. 1).

Figure 2:
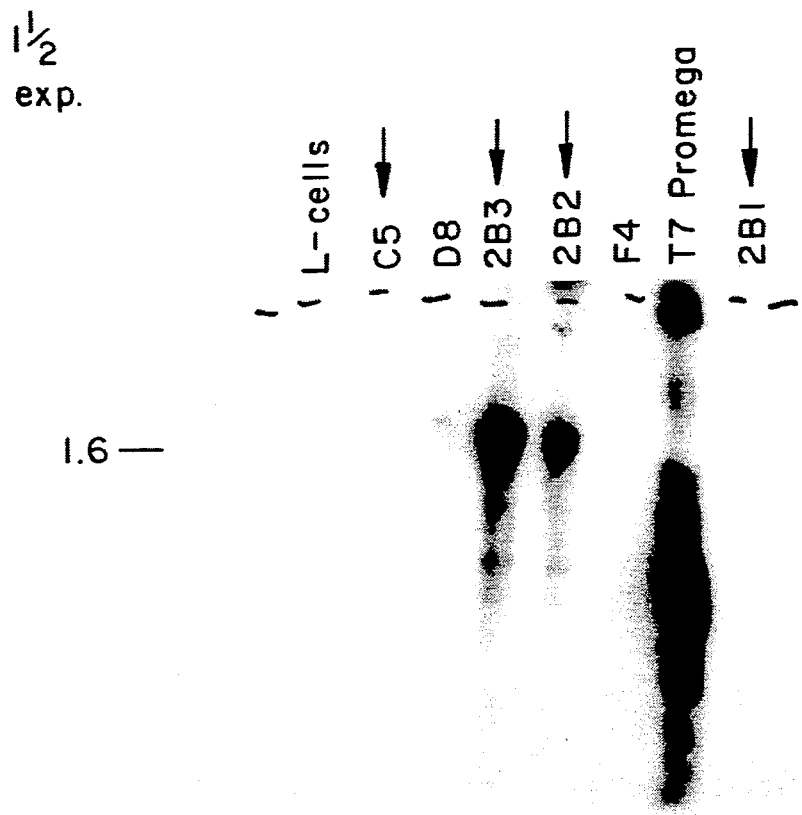
FIG. 2 shows the RNA transcription products formed in the cytoplasmic extracts of clones 2B2 and 2B3 when a DNA template with a T7 promoter was added to the cytoplasmic extracts.

The enzymatic activity of the T7 RNA polymerase in the cytoplasmic extract of the transfected cells was determined by T7 RNA polymerase-specific transcription assay performed in vitro as recommended by Promega-Biotec. 0.6 μg linear pT7EMCAT [Elroy-Stein et al., Proc. Natl. Acad. Sci. USA 86, 6126-6130 (1989)]was used as template, and 3 μl cytoplasmic extract were used instead of purified T7 RNA polymerase, in a total reaction volume of 25 μl. To prepare cytoplasmic extracts, a pellet of $10^6$ cells was suspended in 0.2 ml RSB buffer (10 mM Tris hydrochloride pH 7.6, 10 mM NaCl, 1.5 mM $MgCl_2$, freeze-thawed 3 times and then nuclei were removed by a 5 min spin in a microcentrifuge. The transcription reaction was incubated for 1 hr. at 37° C., ethanol precipitated and analyzed by 4% acrylamide-urea gel electrophoresis (FIG. 2). The analysis revealed that the cytoplasmic extracts of clones #2B2 and #2B3 contained an active T7 RNA polymerase enzyme as it was able to transcribe the DNA template from its T7 promoter, to yield the expected full length RNA (FIG. 2).

Expression of a transfected target gene in T7 RNA polymerase cell line

Figure 3:
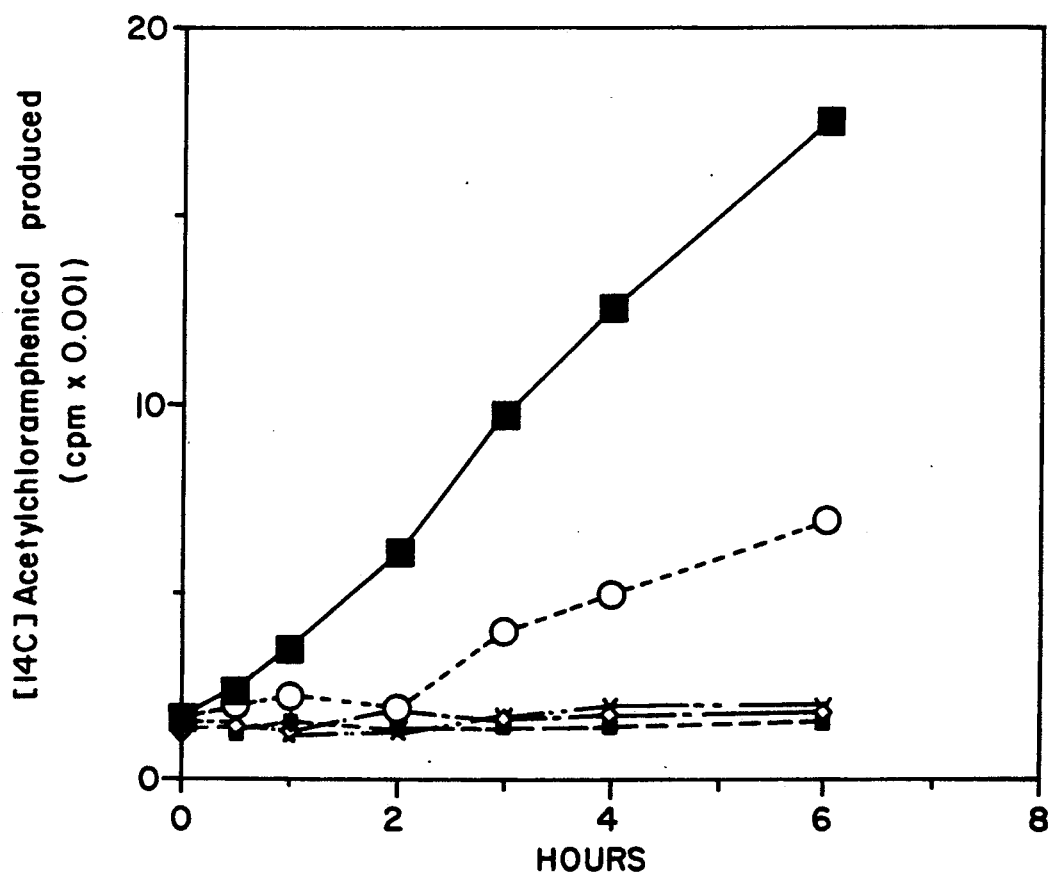
FIG. 3 shows the level of expression of chloramphenicol acetyl transferase (CAT) in either plain L-cells or G418 resistant clones transfected with pT7EMCAT.

The ability of the T7 RNA polymerase-expressing cells to express a target gene which is under the control of T7 promoter and encephalomyocarditis virus (EMCV) untranslated region (UTR) leader was analyzed using chloramphenicol acetyl transferase (CAT) as a reporter gene. Sub-confluent monolayer of $10^6$ cells of either plain L-cells or 4 different G418 resistant clones (#C5, #2B1, #2b2, #2B3) were transfected with 5 μg of supercoiled pT7EMCAT [Elroy-Stein et al., Proc. Natl. Acad. Sci. USA 86, 6126-6130 (1989)], as described before. 48 hrs. later CAT activity was determined by the diffusion-based CAT assay as recommended by Dupont-NEN. As shown in FIG. 3, CAT was not expressed either in L cells nor in clones #C5 and #2B1, which do not express the T7 RNA polymerase enzyme. However, clones #2B2 and #2B3 enabled the transient expression of CAT from a transfected pT7EMCAT plasmid. No expression was obtained when EMCV UTR was not present in the CAT plasmid. The CAT expression level in clone #2B3 was 2-4 times higher then its level when expressed from pRSV-CAT which contains an efficient eukaryotic promoter.

As clone #2B3 enabled higher CAT expression level of pT7EMCAT than did clone #2B2, the first was maintained as the "T7 RNA polymerase expressor cell line" and was termed the "OST7-I cell line". [The OST7-1 cell line (mammalian-mouse L(A9) cells) was deposited under the Budapest Treaty on Feb. 28, 1990 at the American Type Culture Collection, 12301 Parklawn Drive, Rockville, Maryland 20851.]

Expression of a Target Gene in Vaccinia Virus

If the T7 RNA polymerase protein is stable in the cytoplasmic environment of OST7-1 cells, then the vaccinia virus recombinant vT7EMCAT [Elroy-Stein et al., Proc. Natl. Acad. Sci. USA 86, 6126–6130 (1989)]could be used to introduce the T7EMCAT template into the cytoplasm. Since viral infection is more efficient than plasmid transfection, recombinant vaccinia virus should be a more efficient delivery agent of genes regulated by the T7 promoter than transfected plasmids. Furthermore, the vaccinia DNA would be amplified by replication.

Figure 4:
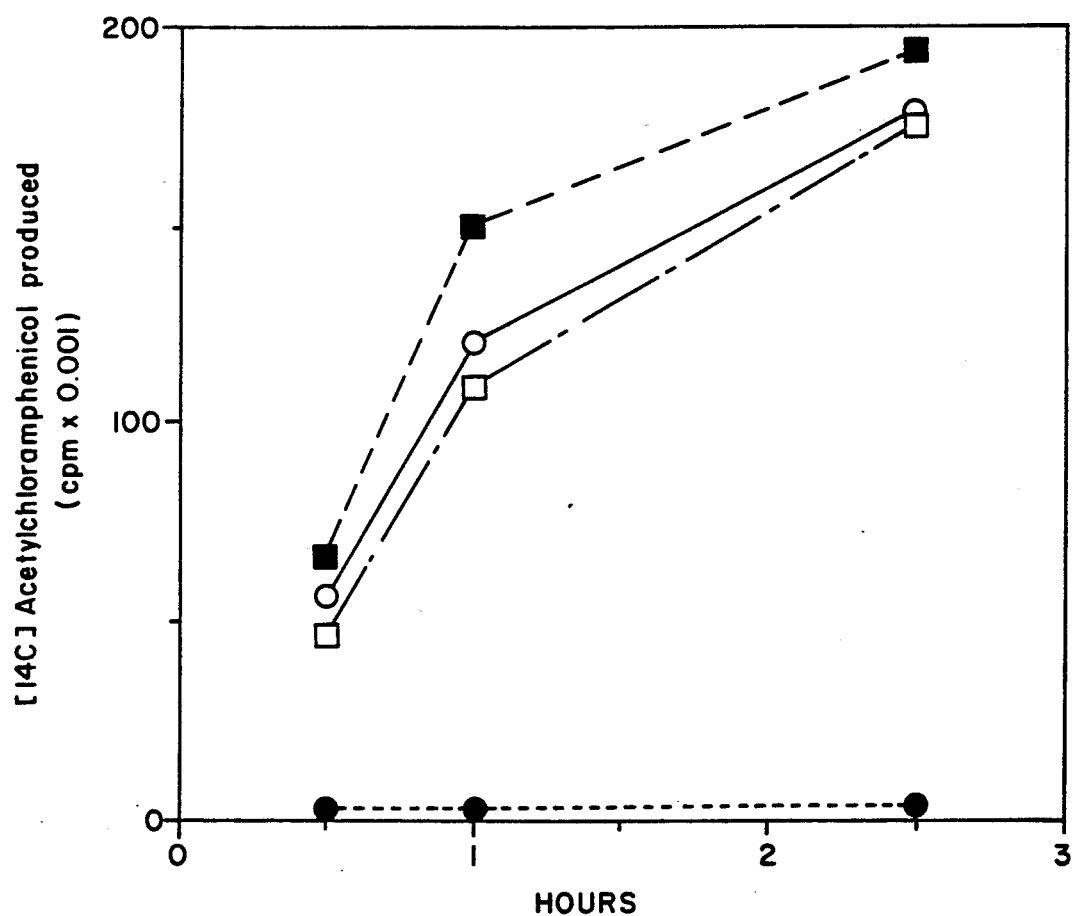
FIG. 4 shows the level of chloramphenicol acetyl transferase (CAT) expression in either plain L-cells or OST7-1 cells infected with vT7EMCAT, wild type vaccinia virus or VT7EMCAT and vTF7-3.

To evaluate the use of recombinant vaccinia virus, $10^6$ cells of either OST7-1 cells or the parental mouse L cells were infected with 20 pfu per cell of vT7EMCAT. As a negative control, cells were infected with wild type vaccinia virus (WR). As a positive control, cells were coinfected with vT7EMCAT and vTF7-3 at a multiplicity of 10 pfu for each virus. 27 hr after infection CAT activity was determined (FIG. 4). As vTF7-3 provides the T7 RNA polymerase [Fuerst et al., J. Mol. Biol. 206, 333–348 (1986)], coinfection of vTF7-3 with vT7EMCAT resulted in high expression of CAT in both cell types, as expected and as discussed before [Elroy-Stein et al., Proc. Natl. Acad. Sci. USA 86, 6126–6130 (1989)]. However, infection of vT7EMCAT alone or with vWR also resulted in a high CAT expression level in OST7-1 cells but not in the parental L-cells (FIG. 4).

Thus, the T7 RNA polymerase enzyme is relatively stable in OST7-1 cells cytoplasm as the anticipated shut-off of host protein synthesis by vaccinia virus did not abolish its activity. This finding provides the opportunity to use only one vaccinia recombinant which contains the target gene under the control of T7 promoter and EMCV UTR and to eliminate the use of the second virus vTF7-3 [ Fuerst et al., J. Mol. Biol. 206, 333–348 (1986)].

The foregoing demonstrates that it is possible to make a stable cell line that expresses a functional T7 RNA polymerase even though it can be toxic to cells. Furthermore, the foregoing demonstrates that stable and functional T7 RNA polymerase transcripts can be made in the absence of vaccinia virus and the cytoplasmic poly (A) polymerase, capping enzymes and other facts provided by the virus. In addition, the foregoing demonstrates that a new cell line can work well in conjunction with vaccinia virus even though the virus is known to shut-off host cell protein synthesis. The above results were unexpected and can not be drawn from the knowledge in the relevant art prior to the present invention.

Using the principles of the present invention, one skilled in the art, without undue experimentation, would be able to establish other eukaryotic cell lines expressing any one of a number of bacteriophage RNA polymerases and would be able to use the cell line for the expression of foreign genes and the production of foreign proteins in eukaryotic cells.

All references cited hereinabove are hereby incorporated in their entirety by reference.

It is understood that the examples and embodiments described herein are for illustrative purposes only and that various modifications or changes in light thereof will be suggested to one skilled in the art and are to be included in the spirit and purview of this application and scope of the appended claims.

What is claimed is:

1. A mammalian cell comprising:
   i) a bacteriophage RNA polymerase gene expressing the polymerase wherein the bacteriophage is selected from the group consisting of T7, SP6, GH1, and T3 ;
   ii) a construct comprising the following elements operably linked:
      a) a promoter recognized by the protein product of said bacteriophage RNA polymerase gene;
      b) a DNA sequence that codes for an untranslated region of a piconnavirus RNA that confers cap independent translation; and
      c) a gene encoding a protein to be expressed.

2. The cell according to claim 1 wherein said bacteriophage gene is a T7 RNA polymerase gene.

3. The cell according to claim 1 wherein said mammalian cells are mouse cells.

4. The cell according to claim 3 wherein said mouse cells are mouse L cells.

5. The cell according to claim 1 wherein said promoter is T7 promoter.

6. The cell according to claim 1 which is OST7-1 cell line.

7. The cell according to claim 1 wherein said untranslated region is from a poliovirus, mengovirus or encephalomyocarditis virus.

8. The cell according to claim 1 wherein said untranslated region is EMCV UTR.

9. A method of expressing a gene in a mammalian cell expressing a bacteriophage RNA polymerase gene, wherein the bacteriophage is selected from the group consisting of T7, SP6, GH1, and T3, which method comprises the steps of:
   introducing into said cell a construct comprising the following elements operably linked:
      a) promoter recognized by the protein product of said RNA polymerase gene;
      b) a DNA sequence that codes for an untranslated region of a cardiovirus RNA that confers cap independent translation; and
      c) a gene encoding a protein to be expressed; and culturing said cell under conditions such that said gene is expressed.

10. The method according to claim 9 wherein said construct is present in a plasmid.

11. The method according to claim 9 wherein said construct is present in a recombinant DNA based cytoplasmic virus.

12. The method according to claim 11 wherein said virus is a poxvirus or a iridovirus.

13. The method according to claim 11 wherein said virus is vaccinia virus.

* * * * *